(12) United States Patent
Stoianovici et al.

(10) Patent No.: US 12,181,269 B2
(45) Date of Patent: Dec. 31, 2024

(54) METHOD OF SIZE MEASUREMENT IN MONO-VISION SCOPE IMAGE

(71) Applicant: THE JOHNS HOPKINS UNIVERSITY, Baltimore, MD (US)

(72) Inventors: Dan Stoianovici, Reisterstown, MD (US); Brian Matlaga, Lutherville, MD (US); Sunghwan Lim, Baltimore, MD (US); Wesley Warren Ludwig, Pikesville, MD (US)

(73) Assignee: The Johns Hopkins University, Baltimore, MD (US)

(*) Notice: Subject to any disclaimer, the term of this patent is extended or adjusted under 35 U.S.C. 154(b) by 765 days.

(21) Appl. No.: 16/642,921

(22) PCT Filed: Aug. 28, 2018

(86) PCT No.: PCT/US2018/048245
§ 371 (c)(1),
(2) Date: Feb. 28, 2020

(87) PCT Pub. No.: WO2019/046237
PCT Pub. Date: Mar. 7, 2019

(65) Prior Publication Data
US 2021/0404796 A1 Dec. 30, 2021

Related U.S. Application Data

(60) Provisional application No. 62/550,872, filed on Aug. 28, 2017.

(51) Int. Cl.
*A61B 1/307* (2006.01)
*A61B 1/00* (2006.01)
(Continued)

(52) U.S. Cl.
CPC .......... *G01B 11/22* (2013.01); *A61B 1/00004* (2013.01); *A61B 1/307* (2013.01);
(Continued)

(58) Field of Classification Search
None
See application file for complete search history.

(56) References Cited

U.S. PATENT DOCUMENTS

| 4,557,255 A | 12/1985 | Goodman |
| 5,047,848 A | 9/1991 | Krauter |

(Continued)

FOREIGN PATENT DOCUMENTS

| EP | 1514226 A2 | 3/2005 |
| EP | 3142572 A1 | 3/2017 |
| WO | 2017120369 A1 | 7/2017 |

OTHER PUBLICATIONS

Patel et al. ("Accuracy of Endoscopic Intraoperative Assessment of Urologic Stone Size"), Journal of Endourology vol. 28, No. 5, May 2014 ᵃ Mary Ann Liebert, Inc. pp. 582-586 (Year: 2014).*

(Continued)

*Primary Examiner* — Randolph I Chu

(57) ABSTRACT

An embodiment in accordance with the present invention provides a method for accurate and objective quantification of stone fragment size. The method includes intraoperative measurement of objects during URS. The method analyzes URS procedures for ureteral and renal stones during basket extraction of fragments. An instrument is passed through an instrument channel of the ureteroscope and advanced until it is adjacent to the stone fragment to be measured. The measurement of stone fragment size is based on the known distance of a tip of the instrument in the ureteroscope's visual field.

9 Claims, 5 Drawing Sheets

(51) Int. Cl.
    *G01B 11/02*     (2006.01)
    *G01B 11/22*     (2006.01)
    *G01B 21/04*     (2006.01)
    *G06T 5/80*     (2024.01)
    *G06T 7/60*     (2017.01)
    *A61B 5/0215*     (2006.01)
    *A61B 5/107*     (2006.01)

(52) U.S. Cl.
CPC ............ *G01B 11/02* (2013.01); *G01B 21/042* (2013.01); *G06T 5/80* (2024.01); *G06T 7/60* (2013.01); *A61B 5/02156* (2013.01); *A61B 5/1079* (2013.01); *G06T 2207/10068* (2013.01)

(56) References Cited

U.S. PATENT DOCUMENTS

| | | | |
|---|---|---|---|
| 7,857,749 | B2 | 12/2010 | Ouchi |
| 9,286,506 | B2 * | 3/2016 | Stevens .................. G06T 7/593 |
| 9,414,806 | B2 | 8/2016 | Bailey et al. |
| 11,039,734 | B2 * | 6/2021 | Hansen .................. G06T 15/08 |
| 2005/0043721 | A1 * | 2/2005 | Ouchi ...................... A61B 10/06 606/1 |
| 2009/0043161 | A1 * | 2/2009 | Doi ...................... A61B 1/00006 600/117 |
| 2012/0289778 | A1 * | 11/2012 | Chan .................... A61B 5/6886 600/109 |
| 2013/0259315 | A1 * | 10/2013 | Angot ...................... G06T 7/12 382/128 |
| 2015/0161802 | A1 * | 6/2015 | Christiansen ........ A61B 5/1076 348/74 |
| 2015/0313444 | A1 | 11/2015 | Wolf |
| 2015/0366571 | A1 | 12/2015 | Navve et al. |
| 2016/0287141 | A1 * | 10/2016 | Sidlesky ............ G02B 23/2415 |
| 2017/0150904 | A1 | 6/2017 | Park et al. |
| 2017/0354320 | A1 * | 12/2017 | Saito ...................... A61B 1/045 |
| 2019/0374155 | A1 * | 12/2019 | Wang .................. A61B 1/2736 |
| 2022/0172390 | A1 * | 6/2022 | Redford .................. G06T 7/593 |

OTHER PUBLICATIONS

Scales, et al., Prevalence of kidney stones in the United States. Eur Urol. Jul. 2012;62(1):160-5.
Oberlin, et al., Contemporary surgical trends in the management of upper tract calculi. J Urol. Mar. 2015;193(3):880-4.
Geraghty, et al., Worldwide Trends of Urinary Stone Disease Treatment Over the Last Two Decades: A Systematic Review. J Endourol. Jun. 2017;31(6):547-556.
De La Rosette, et al., The clinical research office of the endourological society ureteroscopy global study: indications, complications, and outcomes in 11,885 patients. J Endourol. Feb. 2014;28(2):131-9.
Teichman, et al., Use of the holmium: YAG laser for the impacted stone basket. J. Urol. 2000;164:1602-1603.
De La Rosette, et al., Handling and Prevention of Complications in Stone Basketing. European Urology 2006;50:991-999.
Chawla, et al., Effectiveness of high-frequency holmium: YAG laser stone fragmentation: the "popcorn effect". J Endourol. Apr. 2008;22(4):645-50.
Emiliani, et al., Optimal Settings for the Noncontact Holmium:YAG Stone Fragmentation Popcorn Technique. J Urol. Sep. 2017;198(3):702-706.
Allen, et al., Baskets in the kidney: an old problem in a new situation. J Endourol. Sep. 2003;17(7):495-6.
Ansari, et al., Holmium: YAG laser rescue for a stuck stone basket. Int Urology and Nephrology 2002;34(4):463-464.
Tanimoto, et al., Ureteral Avulsion Associated with Ureteroscopy: Insights from the MAUDE Database. J Endourol. Mar. 2016;30(3):257-61.
Ge, et al., Management of complete ureteral avulsion and literature review: a report on four cases. J Endourol. Feb. 2011;25(2):323-6.
Zhang, et al., A Flexible New Technique for Camera Calibration. IEEE Transaction on Pattern Analysis and Machine Intelligence 2000;20(11).

* cited by examiner

METHOD OF SIZE MEASUREMENT IN MONO-VISION SCOPE IMAGE

CROSS REFERENCE TO RELATED APPLICATIONS

This application is a 35 U.S.C. § 371 U.S. national entry of International Application PCT/US2018/048245, having an international filing date of Aug. 28, 2018, which claims the benefit of U.S. Provisional Patent Application No. 62/550,872 filed on Aug. 28, 2017, the content of each of the aforementioned applications is herein incorporated by reference in their entirety.

FIELD OF THE INVENTION

The present invention relates generally to medical imaging. More particularly, the present invention relates to a method of size measurement in mono-vision scope image.

BACKGROUND OF THE INVENTION

Urolithiasis is becoming increasingly prevalent, and flexible ureteroscopy (URS) is a very common treatment modality. URS provides an excellent stone free rate and utilization of this technique has been increasing at a great rate. A common challenge during URS is accurately determining the size of a visualized object. To this end, urologists often use some combination of either comparison to known landmarks or reference to implements of a known size in order to estimate stone dimensions. However, this can be an unreliable metric, particularly for individuals who are less familiar with URS. Currently, there is no purpose-built tool to measure stone size during URS.

The ability to measure stone fragment size is particularly important for intraoperative decision-making. An accurate size measurement determines the need for and extent of further fragmentation, likelihood of spontaneous fragment passage, and ability to safely extract fragments through a ureter or ureteral access sheath. Additionally, underestimation of stone fragment size can lead to complications such as ureteral trauma or an entrapped basket. Misjudging stone size can also result in multiple exchanges of ureteroscopic instruments and discontinuous stone fragmentation which can increase operative time and decrease surgeon productivity.

Mono-vision scope medical systems do not provide the ability to measure objects in the image. Theoretically, the measurements require stereo-vision for depth triangulation. In urology, kidney stone size cannot be accurately measured while performing ureteroscopy (URS).

It is therefore desirable to provide a method to achieve an accurate and objective quantification of stone fragment size.

SUMMARY OF THE INVENTION

The foregoing needs are met, to a great extent, by the present invention, wherein in one aspect a method of the present invention includes using a scope with a lateral instrument channel for the measurement of object size in the scope image.

In accordance with an aspect of the present invention, the method includes passing an instrument through the instrument channel and advancing until it is in contact with the object to be measured. The method includes determining a scale of the object in the image as inversely related to a depth of the instrument. The method includes measuring the depth of the instrument in the scope image. The method includes measuring the depth of the instrument with a device. Further, the method includes calibrating the measurement based on imaging experiments. The method also includes using a non-transitory computer readable medium programmed for executing steps of the method. The method includes calibrating the scope before use for measurement of object size in the scope image. Additionally, the method includes dewarping the scope image before measurement of object size in the scope image. The method also includes calibrating the scope with a checkerboard of squares of a known size, measuring warping of the checkerboard in the scope image, and applying a reverse transformation to dewarp the image.

In accordance with another aspect of the present invention, a method for determining an actual size of an object in an image obtained by a scope includes determining a calibration coefficient for measuring the size of the object in the image. The method includes measuring a perceived size of the object and a depth of the object in the image and dewarping the image. The method also includes calculating the actual size of the object in the image In accordance with still another aspect of the present invention, the method includes calibrating the scope with a checkerboard of squares of a known size, measuring warping of the checkerboard in the scope image, and applying a reverse transformation to dewarp the image. The method includes calculating the actual size of the object in the image using $$\lambda = \frac{s}{S} = \left(-\frac{1}{R}\right)d + \frac{r}{R}.$$

The method includes determining a scale of the object to be measured as inversely related to a depth of the instrument. The method also includes measuring the depth of the object based on distance from an instrument. Additionally, the method includes using a non-transitory computer readable medium programmed for executing steps of the method.

In accordance with yet another aspect of the present invention, a system for determining an actual size of an object in an image includes a scope. The system includes an instrument configured to be advanced to the object. Additionally, the system includes a non-transitory computer readable medium programmed for determining a calibration coefficient for measuring the size of the object in the image. The non-transitory computer readable medium is programmed for measuring a perceived size of the object and a depth of the object in the image. The non-transitory computer readable medium is programmed for dewarping the image and calculating the actual size of the object in the image.

In accordance with another aspect of the present invention, the scope takes the form of a uteroscope. The system includes a checkerboard of squares of a known size for calibrating the uteroscope. The instrument can take the form of one selected from a group of a wire or a basket.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method for accurate and objective quantification of stone fragment size. The method includes intraoperative measurement of objects during URS. The method analyzes URS procedures for ureteral and renal stones during basket extraction of fragments. An instrument is passed through an instrument channel of the ureteroscope and advanced until it is adjacent to the stone fragment to be measured. The measurement of stone fragment size is based on the known distance of a tip of the instrument in the ureteroscope's visual field.

The size of an object viewed in the ureteroscope image depends on its distance from the end of the scope. The distance can be estimated by the depth of a wire that it advanced until it touches the object, and that the depth can be measured from the image. A geometric model, calibration procedure, and software tool were developed to implement the method of the present invention.

With respect to the geometric model, the fact that the size of an object viewed in the image is inversely related to its distance from the scope face is intuitively trivial. The following mathematics are used to determine whether the size of the object viewed in the image is related to the depth of the wire measured in the actual image. Then, this dependency is used for the experimental calibration of the image scale, followed by actual stone measurements.

Figure 1:
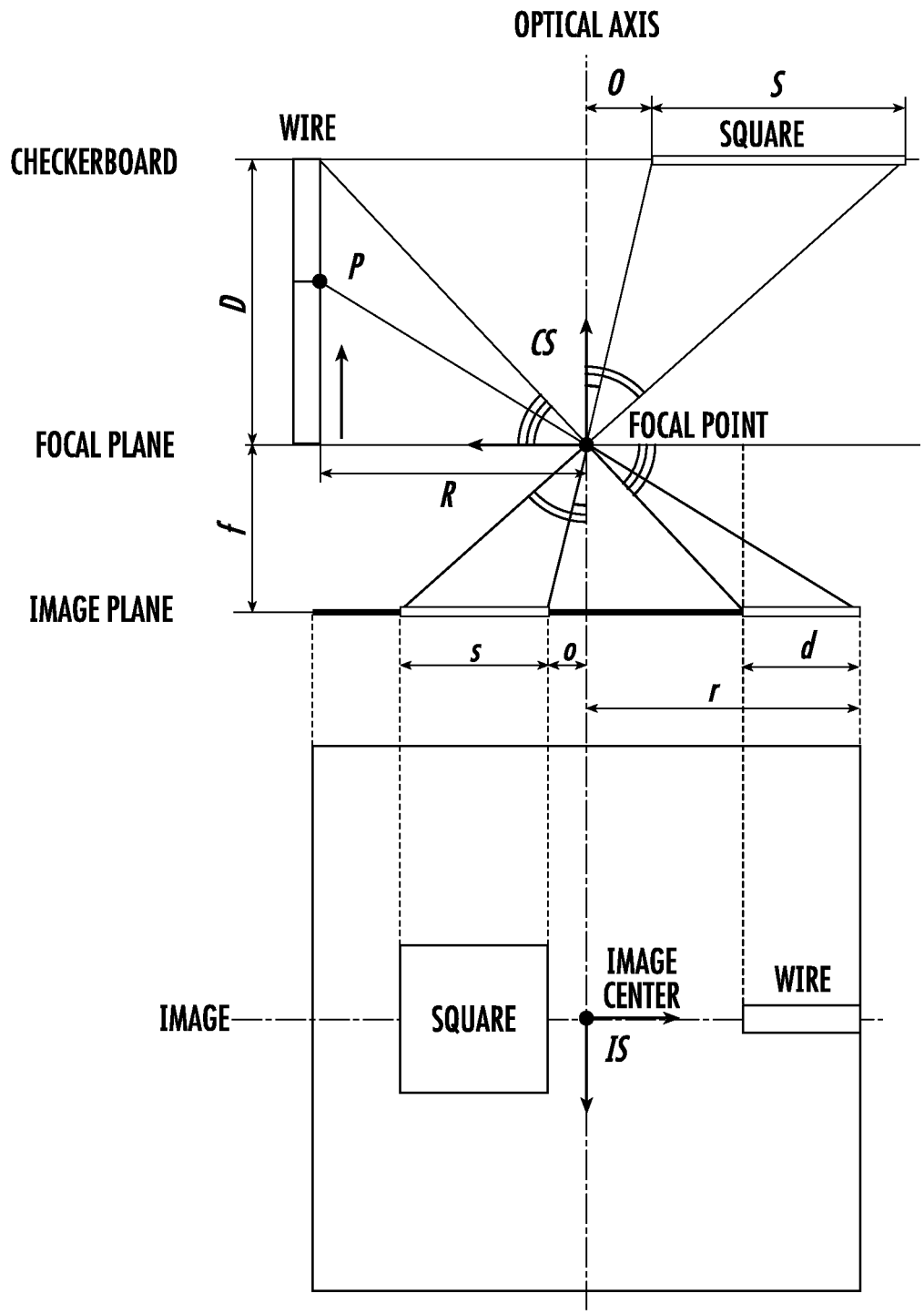
FIG. 1 illustrates a schematic diagram of the method, according to an embodiment of the present invention.
Figure 2A:
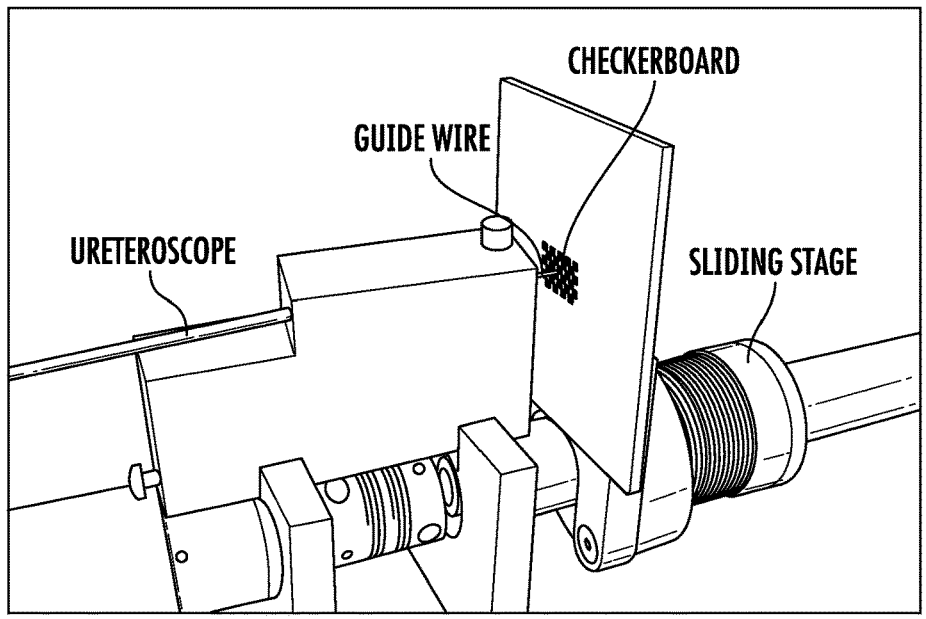
FIGS. 2A-2D illustrate ureteroscope calibration, according to an embodiment of the present invention.
Figure 2B:
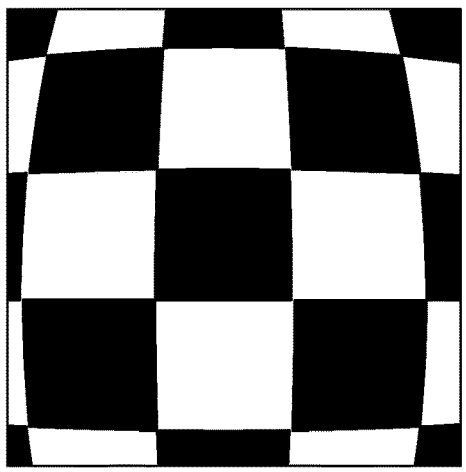
Figure 2C:
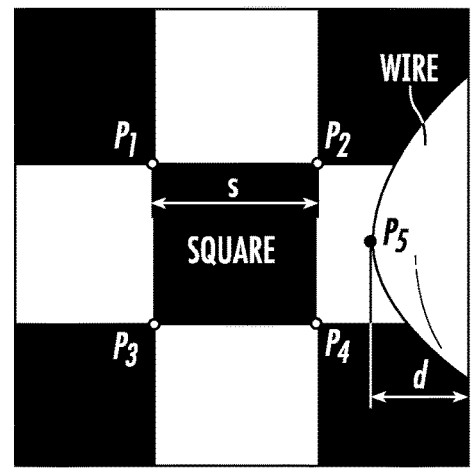
Figure 2D:
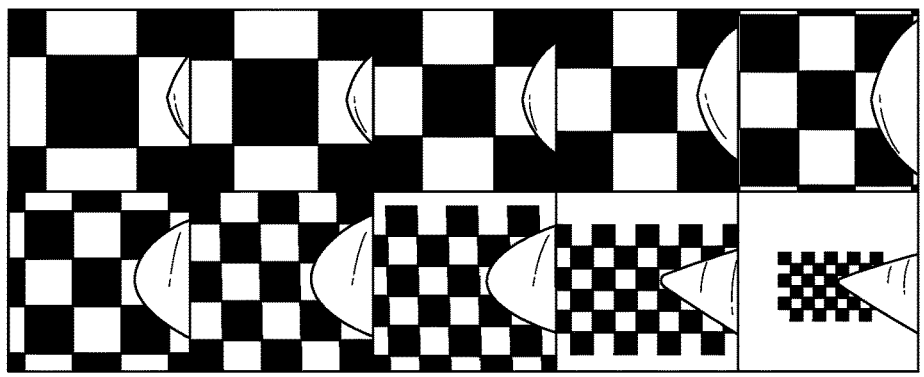

FIG. 1 illustrates a schematic diagram of the method, according to an embodiment of the present invention. As illustrated in FIG. 1, the schematic diagram of the measurement principle includes the physical space (camera space, CS) shown at at the top side and the image space (IS) at the bottom. A checkerboard calibration rig is placed in front of the scope, as illustrated in FIG. 2A. In FIG. 1, a square of the board having the size S [mm] and the horizontal offset of 0 [mm] is shown, at a distance D [mm] from the focal plane. The size of the imaged square is s [pixel] with the offset o [pixel]. FIGS. 2A-2D illustrate ureteroscope calibration, according to an embodiment of the present invention. FIG. 2A illustrates an experimental setup, according to an embodiment of the present invention. FIG. 2B illustrates an original ureteroscopic image (distorted). FIG. 2C illustrates a processed image (undistorted), and FIG. 2D illustrates checkerboard images captured at different positions.

Common ureteroscopes include a wire channel on the side. The distance between the side of the wire and the optical axis is R [mm]. During insertion through the scope, the wire is not initially visible in the image. When advanced deeper, the tip of the wire exits the scope and, at some point P, it appears on the side of the image, as shown in FIG. 2C. The wire is advanced further until it touches the checkerboard at a depth D, as illustrated in FIG. 1. In the image, the wire appears to advance laterally, from the edge towards the center of the image, therefore n the image the depth is measured laterally. Through the projection on the Image Plane (at focal length f [pixel]), the depth of the wire in the image is d [pixel]. The insertion is visible from the side of the image, at a distance r [pixel].

Among the symbols above {D, d, o, s} are variables and other are constant parameters. From 3 pairs of similar triangles (colored), $$\frac{O}{o} = \frac{D}{f} \Rightarrow o = O\frac{f}{D} \tag{1}$$

$$\frac{O+S}{o+s} = \frac{D}{f} \Rightarrow s = (O+S)\frac{f}{D} - o = S\frac{f}{D} \tag{2}$$

$$\frac{D}{f} = \frac{R}{r-d} \Rightarrow D = \frac{Rf}{r-d} \tag{3}$$

By substitution, $$s = S\frac{r-d}{R} = \left(-\frac{S}{R}\right)d + \frac{Sr}{R} \tag{4}$$

The scale of the image λ [pixel/mm] is, $$\lambda = \frac{s}{S} = \left(-\frac{1}{R}\right)d + \frac{r}{R} \tag{5}$$

This shows that the scale of the objects in the image (λ) is inversely relate $$\left(-\frac{1}{R}\right)$$

to the depth to the object measured in the image (d), with an offset $$\left(\frac{r}{R}\right).$$

With respect to calibration, the experimental setup is shown in FIG. 2A. A single-use ureteroscope (Lithovue, Boston Scientific) and a guide-wire (⌀0.965 mm, Hydro-Glide, Bard) were used. The end of the scope was fixed on the test device. A checkerboard (8×6 with S=11/8 mm) was mounted to a linear sliding stage aligned with the optical axis of the scope, as shown in FIG. 2A. Images from the scope were acquired to a PC with a video capture device (AV.io HD, Epiphan Systems, Canada) from the DVI output of the scope machine.

Typical images of scopes are radially distorted, as shown in FIG. 2B. Because the geometric model above assumes an undistorted perspective view, the first step of the calibration is to dewarp the image. Distortion correction was performed with a common technique, and any technique known to or conceivable to one of skill in the art can be used. In short, the warping was measured based on the images of the checkerboard, and a reverse transformation was applied to dewarp it, as shown in FIG. 2C. Dewarping is then applied in real-time to the images acquired.

The slope and offset coefficients in Equation 5 depend on the constant parameters $\{R, r\}$. However, these may be difficult to measure directly. Instead, a calibration is performed to identify them experimentally. The checkerboard was translated to 10 locations ($D_i$, i=1, ..., 10), and its images were captured at each position, as shown in FIG. 2D. From each image, the corner points of a checkerboard square ($p_{1_i}$, $p_{2_i}$, $p_{3_i}$, $p_{4_i}$) and the tip point of the wire ($p_{s_j}$) were selected, as shown in FIG. 2C. The size of the square ($s_i$) was calculated as the average length of its four sides. The distance $d_t$ was measured from the point of the wire to the right edge of the screen, as shown in FIG. 2C. The image scale was calculated for each experiment as $$\lambda_i = \frac{s_i}{S}.$$

These were plotted versus the distance $d_i$, and a linear interpolation was used to determine the two slope and offset coefficients. The entire calibration was repeated with a second ureteroscope of the same kind, to compare the results. The coefficients determined for each scope were averaged ($R=(R_1+R_2)/2$ and $r=(r_1+r_2)/2$) and used for the measurements. Note that interpolating the experimental points from both scopes would yield similar coefficients.

With respect to measurement, the calibration coefficients were used to measure the size of objects (stones) in the image: 1) advance a wire or instrument to the object, 2) measure the size of the object (s) and the depth (d) in the image, and 3) calculate the actual size (S) based on Eq. 5.

For an experimental implementation of the present invention, software was developed in Visual Studio 2017 (C++, Microsoft Corp.) with open source computer vision library (OpenCV). Any software implementation known to or conceivable to one of skill in the art for the implementation of the method of the present invention could be used. The software implements the distortion correction and measurement methods described above. A scale was represented on the sides of the image as shown in FIGS. 3B and 3D, that changes according to the depth D.

Figure 3A:
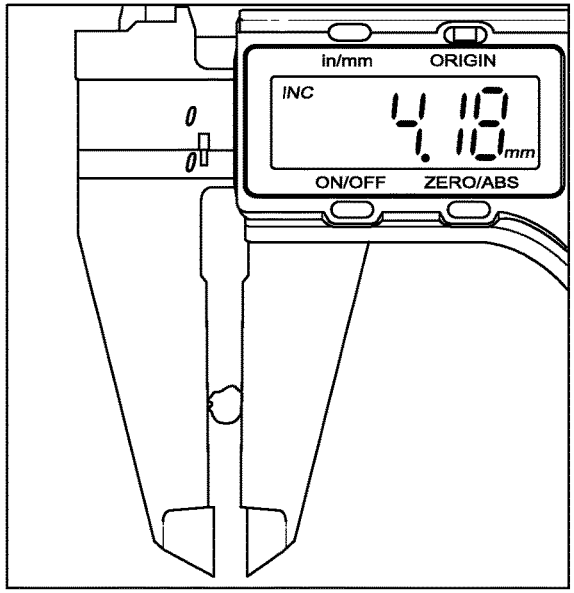
FIGS. 3A-3D illustrate images of a method of stone measurement, according to an embodiment of the present invention.
Figure 3B:
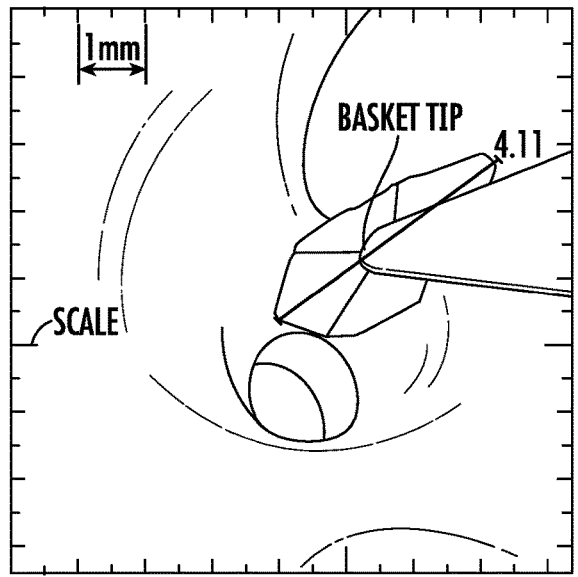
Figure 3C:
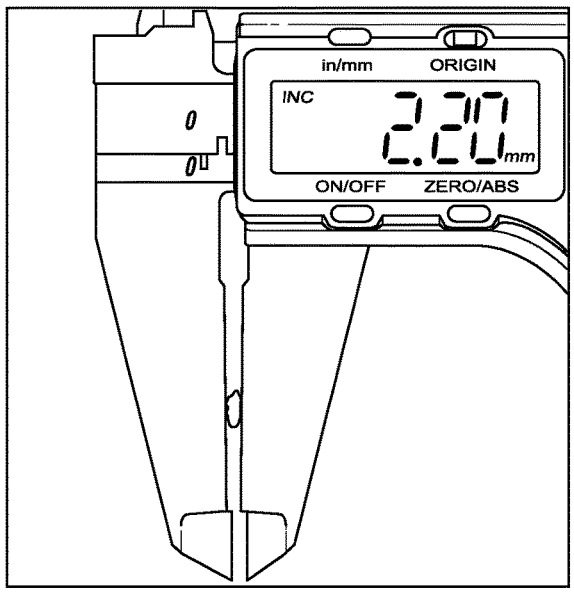
Figure 3D:
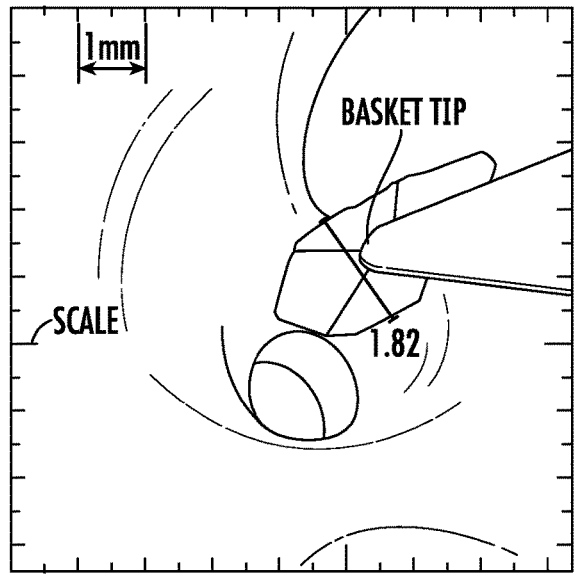

FIGS. 3A-3D illustrate images of a method of stone measurement, according to an embodiment of the present invention. FIGS. 3A and 3C illustrate a stone fragment as measured by digital calipers. FIGS. 3B and 3D illustrate the same stone fragment as measured by software. The fragment is grasped within the basket and the basket tip serves as the reference point for stone measurement. A scale can be seen around the periphery of the image, with a 1 mm measurement marked in yellow. The stone fragment can also be measured by selecting the limits of the stone (with corresponding stone measurement of 4.11 and 1.82 mm).

An exemplary implementation of the present invention was performed in order to demonstrate the method of the present invention. This exemplary implementation is not meant to be considered limiting and any way of implementing the present invention, known to or conceivable to one of skill in the art could also be used. In an IRB-approved study, URS was performed for ureteral and renal stones per standard of care in four patients over the age of 18 without identified genitourinary abnormality. A new single-use digital ureteroscope of the same model employed for the calibration was used in each case. Stones were fragmented with a 200-micron laser fiber and a 1.9 French Zero Tip nitinol stone retrieval basket (Boston Scientific) was used for stone extraction. Recordings were obtained throughout the duration of each ureteroscopic case—starting with rigid cystoscope insertion and terminating with ureteral stent placement. A ureteral access sheath (Navigator HD, 11/13 French, Boston Scientific) was used in one case in which numerous renal stones were present. Immediately following extraction, fragments were numbered and digital calipers (Mitutoyo CD-8"CSX, Japan) were used to measure the longitudinal ($S_l$) and transversal ($S_t$) axes of the stone, as shown in FIGS. 3A and 3C. Caliper measurement provided the gold-standard measurement for comparison to the software-acquired stone measurements.

The recorded images were analyzed after the procedure. The size of the stone from the images was measured while the stone fragment was within the endoscopic basket, as shown in FIGS. 3B and 3D and the entire stone and basket were visible. The workflow of the software program requires that the user select a portion of the basket in contact with the stone to measure d and calibrate the image scale. This scale then becomes visible around the periphery of the image and can be used for future measurement reference, as seen in FIGS. 3B and 3D. Following this step, measurements can either be performed using the visible scale or selection of the object sides. The longitudinal ($s_l$) and transversal ($s_t$) sizes of the stone were measured for all stones, as shown in FIGS. 3B and 3D.

Measurement errors were calculated as the difference between the software and caliper measured sizes in mm, for both the longitudinal and transversal measurements, as:

$$E_l = \frac{s_l}{\lambda} - S_l \qquad (6)$$
$$E_t = \frac{s_t}{\lambda} - S_t$$

The accuracy and precision of measurements were calculated as the average and standard deviation of the errors over the entire dataset, as usual. Additionally, confidence intervals and Pearson's correlation coefficients were calculated for corresponding measurements. Analyses were performed using R version 3.1.2. A p-value <0.05 was considered statistically significant.

Figure 4:
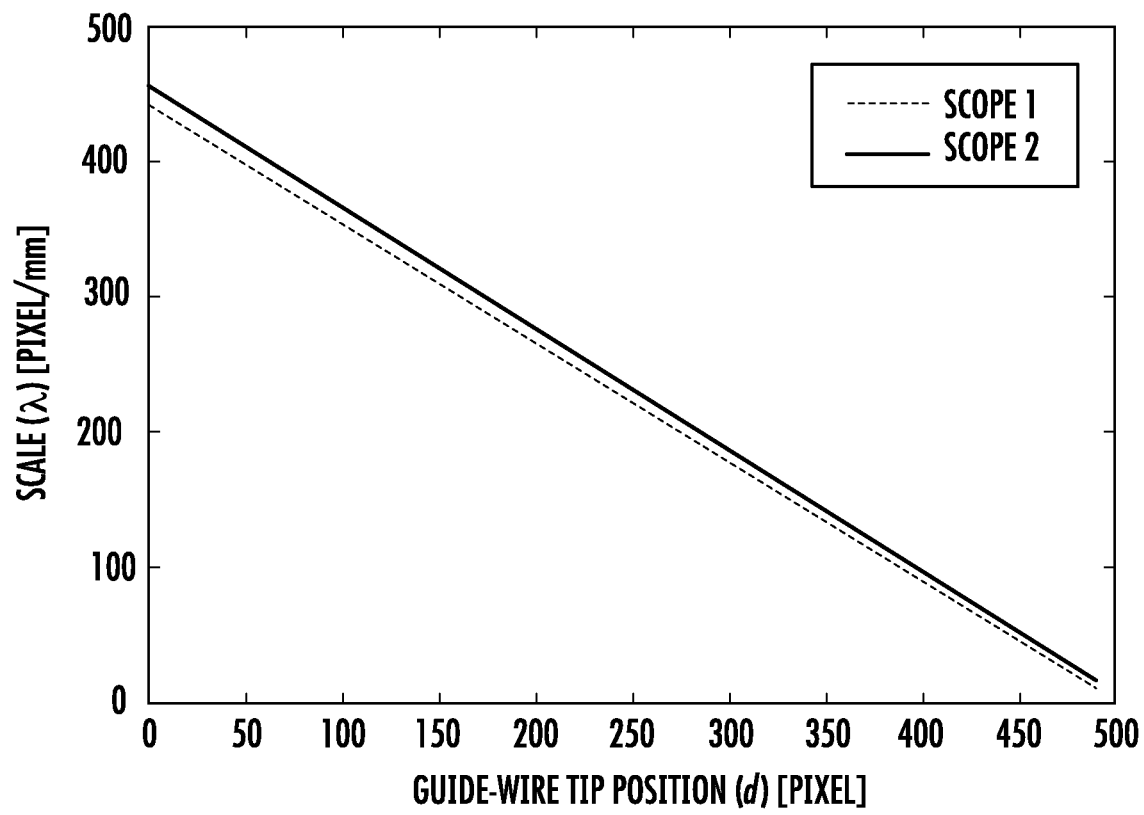
FIG. 4 illustrates a graphical view of calibration results of two ureteroscopes.

FIG. 4 illustrates a graphical view of calibration results of two ureteroscopes. Dark grey and light grey asterisks indicate the measurement values of the scopes. The line indicates the results of a linear regression. FIG. 4 shows the linear regression results of the ureteroscopes. The two constant parameters, are $R_1$=1.135 [mm] and $r_1$=501 [pixel] for Scope 1 and $R_2$=1.115 [mm] and $r_2$=508.2 [pixel] for Scope 2. Their respective average parameters are R=1.125 [mm] and r=504.6 [pixel]. These values were used in the measurements.

Figure 5A:
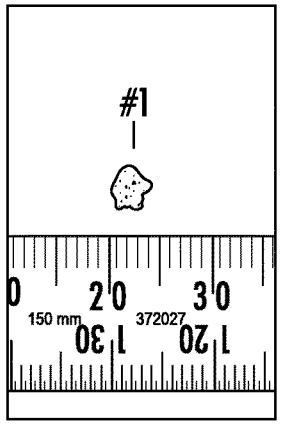
FIGS. 5A-5D illustrate image views of stone fragments from patient 1 (FIG. 5A), patient 2 (FIG. 5B), patient 3 (FIG. 5C), and patient 4 (FIG. 5D).
Figure 5B:
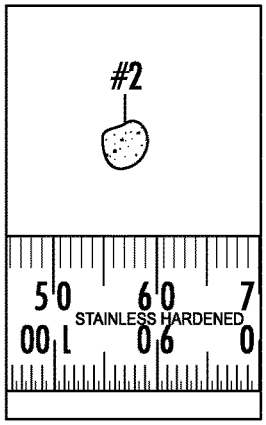
Figure 5C:
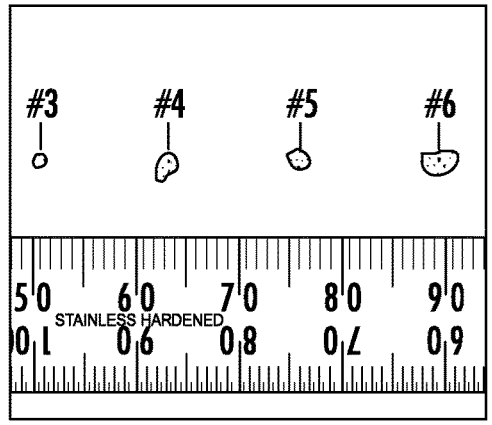
Figure 5D:
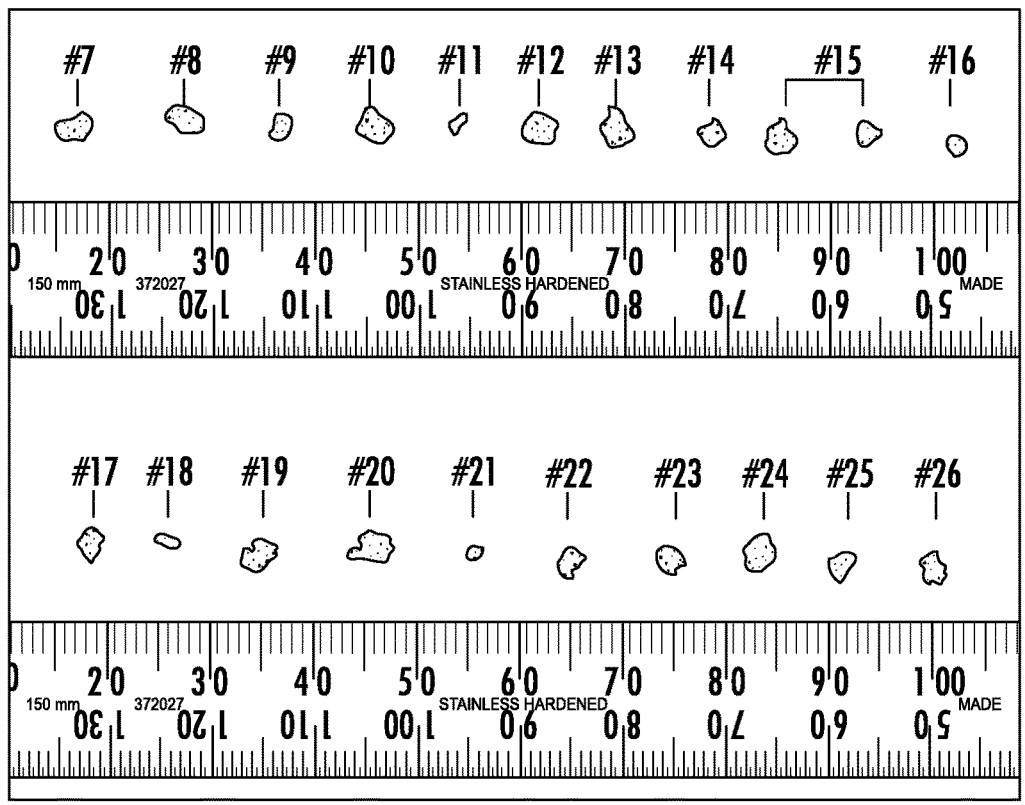

URS was performed for 17 stones in four patients, which resulted in 26 measured stone fragments, as illustrated in FIGS. 5A-5D, and 52 longitudinal and transversal measurements. FIGS. 5A-5D illustrate image views of stone fragments from patient 1 (FIG. 5A), patient 2 (FIG. 5B), patient 3 (FIG. 5C), and patient 4 (FIG. 5D). Patient and stone characteristics can be seen in Table 1. The median stone size was 3.0±1.9 mm, with the largest stone measuring 7.3 mm. All stone fragments saved for analysis could be measured and no technical difficulties were encountered with this task. The longitudinal and transversal stone fragment measurements obtained by software and caliper measurement are listed in Table 2. The median longitudinal and transversal stone fragment size as measured by digital calipers were 3.2±0.8 mm and 2.2±0.6 mm, respectively. The median longitudinal and transversal stone fragment size measurements determined by the software were 3.2±0.8 mm and 1.9±0.7 mm, respectively. The median longitudinal and transversal error was 0.14 mm (95% CI 0.09-0.19) and 0.09 mm (95% CI 0.01-0.16), respectively. The maximum errors measured for longitudinal and transversal measurements were 0.53 and 0.59 and the minimum measured were 0.02 and 0.01 mm.

The longitudinal and transversal accuracy of measurement were 0.18 and 0.18 mm, for an overall accuracy of 0.18 mm. The longitudinal and transversal precision to measure stone fragments were 0.12 and 0.18 mm, for an overall precision of 0.16 mm. The longitudinal and transversal measurements obtained by the software and digital calipers were highly correlated (r=0.97 and 0.92, respectively). Stone size was not correlated with longitudinal and transversal error measurement (r=0.3 and 0.1, respectively). Additionally, there were no statistically significant differences between errors measured in calcium oxalate and cystine stones (p=0.2).

The software of the present invention proved to be accurate and precise, with a median error less than 0.15 mm. Software measurements were highly correlated with standard measurement using digital calipers and there was no correlation between stone fragment size and error measured. Thus, this software can be used with a high degree of reliability, accuracy and precision during URS.

A limitation of the study was that the calibration was only performed with two scopes. Based on the accurate measurements performed with 4 other scopes it appears that the calibration coefficients are relatively constant. Because calibrating the actual single-use scope before the case is not feasible, one has to relay on previously derived calibration results, and scopes should have uniform characteristics. Testing a larger number of scopes and possibly setting uniform calibration characteristic among other manufacturing controls of the scopes would be helpful.

The experimental implementation used single-use ureteroscopes. The calibration and measurement methods, however, are readily applicable to reusable ureteroscopes and other types of scopes. In case of reusable scopes, it is possible to perform the calibration individually, if needed.

In the method of the present invention and the corresponding experiments the depth of the wire was estimated based on the view of the visible part of the wire in the images. The advantage of this approach is that it does not require additional hardware. An alternative approach is to employ a wire tracking device, such as a wire roller or spool that could measure the depth of the wire tip in real time, to adjust the scale of the images in the plane of the wire point.

The ability to determine stone size during URS is both clinically relevant and commonly useful. An application of this technology is in assisting the determination of fragmentation completeness. This is particularly true as the "dusting" technique is increasingly used in URS. Dusting relies on laser settings of a high frequency and low energy; this will fragment the stone into small pieces, or "dust", which are then spontaneously discharged from the kidney. However, without an accurate measure of fragment size, assumptions about stone passage may be erroneous. At other points during URS, particularly during basket extraction of fragments, stone size estimation is also required. Attempting to basket a particularly large stone can lead to stone impaction, necessitating multiple additional manipulations and significant case prolongation. Importantly, attempting to remove a larger than anticipated stone can lead to substantial ureteral complications, including; injury, intussusception and avulsion. Severe ureteral injuries often require reconstructive procedures and are associated with major morbidities and changes in quality of life. Understanding stone fragment size can also potentially decrease operative time, as extraction would commence only once all fragments were small enough to be effectively removed.

A limitation of the current study is that it was performed on URS video footage, as opposed to occurring in real-time. This was performed to determine the safety, feasibility, and accuracy of the measurement, prior to intraoperative measurement trials to follow. Although rare, some fragment measurements had greater levels of error—up to 0.5 mm of inaccuracy. This could lead to an occasional imprecise measurement, but it remains to be determined if that is clinically relevant. Future studies will attempt to determine causative or predictive factors of stone measurement error. A foreseeable cause is the relative position of touching the stone with the wire that may require clinical training.

Once this application can be utilized concurrently with existing endoscopic video equipment, an evaluation of its broader intraoperative performance will be undertaken. While stones were only measured while basketing, measurements can also be performed using other endoscopic instruments. Future studies will investigate measurements obtained using laser fibers or other ureteroscopic instruments to confirm similar results. Additional ureteroscope types, such as the more commonly used reusable fiber-optic and digital ureteroscopes will also be tested to confirm that accuracy and precision is maintained across ureteroscope type.

This study describes a novel method and software application to measure the stone fragment size during URS. It is believed that no mono-vision scope medical system provides the ability to measure objects in the image. Theoretically, the measurements require stereo-vision for depth triangulation. However, it is observed with the present invention, demonstrated mathematically, and verified experimentally that the mono-vision measurement is possible with the help or a wire or other instrument advanced to the object that is used as a surrogate of the missing depth information.

The accuracy and precision of the software were less than 0.19 mm, and the measurements between the software and digital calipers were highly correlated. The software's ease of use may permit its application to other types of endoscopy. Indeed, this could prove to be a useful tool for measuring not only stones, but also findings during cystoscopy, colonoscopy or laryngoscopy/bronchoscopy. Accurate and precise real-time endoscopic measurements would be of benefit to the entire medical community.

TABLE 1

Demographic and stone characteristics of patients undergoing URS (n = 4).

| | |
|---|---|
| Age (median) | 63 ± 13.9 |
| Sex | Male: 4 (100%) |
| BMI | 23 ± 2.9 |
| Race | Caucasian: 4 (100%) |
| History of previous URS | 2 (50%) |
| Side | Left: 1 (25%) |
| | Right: 2 (50%) |
| | Bilateral: 1 (25%) |
| Location | Ureteral: 2 (50%) |
| | Renal: 2 (50%) |
| Pre-stented | 2 (50%) |
| Ureteral access sheath used | 1 (25%) |
| Stone composition | Calcium oxalate: 3 (75%) |
| | Cystine: 1 (25%) |

TABLE 2

Longitudinal and transversal measurements for each stone fragment as measured by digital calipers and software, with listed errors. All measurements in mm.

| | Distance | Longitudinal [mm] | | | Transversal [mm] | | |
|---|---|---|---|---|---|---|---|
| Fragment # | d [pixel] | Caliper | Software | Error | Caliper | Software | Error |
| 1 | 343 | 3.98 | 4.03 | 0.05 | 3.32 | 3.38 | 0.06 |
| 2 | 373 | 4.18 | 4.11 | 0.07 | 2.20 | 1.82 | 0.38 |
| 3 | 266 | 1.49 | 1.55 | 0.06 | 1.22 | 1.28 | 0.06 |
| 4 | 326 | 2.39 | 2.65 | 0.26 | 1.78 | 1.79 | 0.01 |
| 5 | 331 | 1.95 | 2.17 | 0.22 | 1.63 | 1.59 | 0.04 |
| 6 | 396 | 3.86 | 3.76 | 0.10 | 2.56 | 2.63 | 0.07 |
| 7 | 250 | 3.66 | 3.33 | 0.33 | 1.92 | 1.81 | 0.11 |
| 8 | 299 | 3.76 | 3.23 | 0.53 | 2.19 | 1.80 | 0.39 |
| 9 | 247 | 3.14 | 2.95 | 0.19 | 1.67 | 1.73 | 0.06 |
| 10 | 362 | 3.52 | 3.22 | 0.30 | 2.54 | 2.58 | 0.04 |
| 11 | 315 | 2.23 | 2.37 | 0.14 | 1.74 | 1.17 | 0.57 |
| 12 | 342 | 3.64 | 3.54 | 0.10 | 3.05 | 2.97 | 0.08 |
| 13 | 402 | 4.15 | 4.44 | 0.29 | 2.74 | 3.28 | 0.54 |
| 14 | 291 | 2.63 | 2.68 | 0.05 | 2.08 | 1.90 | 0.18 |
| 15 | 125 | 3.23 | 3.37 | 0.14 | 3.21 | 3.09 | 0.12 |
| 16 | 310 | 2.58 | 2.35 | 0.23 | 1.48 | 1.44 | 0.04 |
| 17 | 315 | 3.63 | 3.71 | 0.08 | 2.34 | 2.53 | 0.19 |
| 18 | 302 | 2.50 | 2.19 | 0.31 | 1.05 | 1.02 | 0.03 |
| 19 | 390 | 4.03 | 3.69 | 0.34 | 2.38 | 2.48 | 0.10 |
| 20 | 365 | 4.84 | 4.52 | 0.32 | 2.94 | 2.88 | 0.06 |
| 21 | 240 | 1.91 | 1.93 | 0.02 | 1.58 | 1.51 | 0.07 |
| 22 | 348 | 2.92 | 2.75 | 0.17 | 1.96 | 1.89 | 0.07 |
| 23 | 272 | 3.22 | 3.17 | 0.05 | 2.40 | 2.49 | 0.09 |
| 24 | 318 | 2.45 | 2.39 | 0.06 | 2.22 | 1.63 | 0.59 |
| 25 | 402 | 3.88 | 3.79 | 0.09 | 2.06 | 2.28 | 0.22 |
| 26 | 254 | 2.43 | 2.33 | 0.10 | 2.30 | 1.82 | 0.48 |

It should be noted that the software of the present invention can be executed with a program(s) fixed on one or more non-transitory computer readable medium. The non-transitory computer readable medium can be loaded onto a computing device, server, imaging device processor, smartphone, tablet, phablet, or any other suitable device known to or conceivable by one of skill in the art.

It should also be noted that herein the steps of the method described can be carried out using a computer, non-transitory computer readable medium, or alternately a computing device, microprocessor, or other computer type device independent of or incorporated with an imaging or signal collection device. An independent computing device can be networked together with the ureteroscope either with wires or wirelessly. The computing device for executing the present invention can be a completely unique computer designed especially for the implementation of this method. Indeed, any suitable method of analysis known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for determining an actual size of an object in an image obtained by a scope comprising:
   receiving image data for the image with a processor, wherein the image data is obtained with the scope in real-time;
   receiving data related to a distance between an instrument and the object, wherein the instrument is advanceable to the object after the scope is stationary;

determining the distance between the object and the scope from the data related to the distance between the instrument and the object;

determining from the image data and the distance between the object and the scope, using the processor, a calibration coefficient for measuring the actual size of the object in the image;

measuring a perceived size of the object and a depth of the object in the image;

dewarping the image to create dewarped image data and a dewarped image;

calculating the actual size of the object in the dewarped image using the dewarped image data and the calibration coefficient; and providing and displaying, in real-time, the actual size of the object and feedback regarding manipulation of and/or removal of the object.

2. The method of claim 1 further comprising:

calibrating the scope with a checkerboard of squares of a known size;

measuring warping of the checkerboard in the scope image; and applying a reverse transformation to dewarp the scope image.

3. The method of claim 1 further comprising determining a scale of the object to be measured as inversely related to a depth of the instrument.

4. The method of claim 1, further comprising measuring the depth of the object based on distance from an instrument.

5. The method of claim 1 further comprising using a non-transitory computer readable medium programmed for executing steps of the method.

6. A system for determining an actual size of an object in an image comprising:

a scope, wherein the scope is configured to transmit image data;

an instrument configured to be advanced to the object, such that a distance between the object and the scope can be determined, and wherein the instrument is advanceable to the object even after the scope is stationary;

a processing device configured with processor executable instructions to perform operation comprising:

receiving data from the scope wherein the data comprises the image;

receiving data related to a distance between the instrument and the object;

determining the distance between the object and the scope from the data related to the distance between the instrument and the object;

determining a calibration coefficient for measuring the actual size of the object in the image from the image data and the distance between the object and the scope;

measuring a perceived size of the object and a depth of the object in the image;

dewarping the image to create dewarped image data and a dewarped image;

calculating the actual size of the object in the dewarped image using the calibration coefficient; and providing and displaying, in real-time, the actual size of the object and feedback regarding manipulation of and/or removal of the object.

7. The system of claim 6 further comprising the scope taking the form of a uteroscope.

8. The system of claim 6 further comprising a checkerboard of squares of a known size for calibrating the uteroscope.

9. The system of claim 6 wherein the instrument comprises one selected from a group consisting of a wire or a basket.

* * * * *